United States Patent
Barkan et al.

(10) Patent No.: US 7,148,208 B2
(45) Date of Patent: Dec. 12, 2006

(54) PHARMACEUTICAL COMPOSITIONS FOR HEADACHE, MIGRAINE, NAUSEA AND EMESIS

(75) Inventors: Raphael Barkan, Zion (IL); Alexander Mirimsky, Rehovot (IL)

(73) Assignee: Meditor Pharmaceuticals Ltd., Rehovot (IL)

( * ) Notice: Subject to any disclaimer, the term of this patent is extended or adjusted under 35 U.S.C. 154(b) by 289 days.

(21) Appl. No.: 10/382,217

(22) Filed: Mar. 5, 2003

(65) Prior Publication Data
US 2004/0006044 A1  Jan. 8, 2004

Related U.S. Application Data

(63) Continuation of application No. PCT/IL01/00817, filed on Aug. 30, 2001.

(60) Provisional application No. 60/229,812, filed on Sep. 5, 2000.

(30) Foreign Application Priority Data

Jul. 30, 2001 (IL) ...................................... 144632

(51) Int. Cl.
*A61K 31/105* (2006.01)
*A61K 31/145* (2006.01)
*A61K 31/535* (2006.01)
*A61K 31/425* (2006.01)
*A61K 31/17* (2006.01)
*A61K 31/715* (2006.01)
*A61K 31/66* (2006.01)

(52) U.S. Cl. ...................... 514/54; 514/114; 514/227.5; 514/237.8; 514/252.12; 514/331; 514/365; 514/374; 514/400; 514/408; 514/580

(58) Field of Classification Search ............... 514/54, 514/114, 227.5, 237.8, 252.12, 331, 365, 514/374, 400, 408, 580
See application file for complete search history.

(56) References Cited

U.S. PATENT DOCUMENTS 4,382,928 A    5/1983  Abblard et al. .............. 424/211
6,160,008 A   12/2000  Mizrakh et al. ............ 514/508

FOREIGN PATENT DOCUMENTS

WO    WO 98/13036         4/1998
WO    WO 98/09653 A1  *  5/1998
WO    WO 98/19674 A2  *  5/1998

OTHER PUBLICATIONS

CAPLUS Accession No. 1978:400302 Effect of radioprotectants administered by inhalation, Zherebchenko et al. Meditsinskaya Radiologiya (1978) 23(2) English abstract.*

* cited by examiner

*Primary Examiner*—Ardin H. Marschel
*Assistant Examiner*—Donna Jagoe
(74) *Attorney, Agent, or Firm*—Winston & Strawn LLP

(57) ABSTRACT

S-alkylsiothiouronium derivatives such as S-ethylisothiouronium diethylphosphate are used for the treatment of headaches, in particular, migraines, as well as for the prevention or treatment of nausea and vomiting. The compositions of the invention are also effective in preventing or alleviating emesis associated with migraines or other medical conditions such as chemotherapy or radiotherapy, as well as other symptoms of migraines including phonophobia and photophobia.

24 Claims, No Drawings

PHARMACEUTICAL COMPOSITIONS FOR HEADACHE, MIGRAINE, NAUSEA AND EMESIS

This application is a continuation of the US national stage designation of International Application PCT/IL01/00817 filed Aug. 30, 2001, the content of which is expressly incorporated herein by reference thereto, and which claims the benefit of U.S. provisional application 60/229,812 filed Sep. 5, 2000.

FIELD OF THE INVENTION

The present invention relates to the use of S-alkyl-isothiouronium derivatives, including, but not limited to, S-ethylisothiouronium diethylphosphate, for the prevention or treatment of headache, including but not limited to migraine, and for the prevention or treatment of emesis, and more particularly, to the alleviation of migraine symptoms, including but not limited to headache, nausea and vomiting.

BACKGROUND OF THE INVENTION

Headache is a term used to describe a varied set of symptoms, ranging in intensity from mild discomfort to the very severe syndrome known by the name of migraine.

While the most severe and debilitating form of headache is migraine headache there are several other types of headaches that warrant consideration in terms of prevalence, including but not limited to premenstrual syndrome (PMS) associated headaches and the condition associated with morning after alcohol consumption, commonly referred to as hangover. Symptoms such as headache, fever, chills, nausea, muscle and nerve pain, lethargy, and others are often manifested during the syndrome known as hangover.

While not life-threatening conditions, both PMS and hangover can be very unpleasant, as well as detrimental on the job or at home. Currently, the most common methods of treating these conditions include self-administration of NSAIDs, painkillers, and other prescription and OTC drugs.

The following publications provide some background art relating to headaches in general and migraines in particular, their causes and their modes of treatment:

1. Capobianco "An overview of the diagnosis and pharmacologic treatment of migraine" Mayo Clin. Proc. (1996) 71:1055–1066.

2. Cohen "Migraine Headache and the Managed Care Formulary" Drugs Benefit Trends (1996) 8(8) 28–30, 33–34, 41.

3. Diamond, "Do Non-Steroidal Anti-Inflammatory Agents Have a Role in the Treatment of Migraine Headaches" Drugs (1989) 37:755–760.

4. Klapper, "Toward a standard drug formulary for the treatment of headache" Headache (1995) April, 225–227.

5. Kumar, "Recent advances in the acute management of migraine and cluster headaches" Journal of General Internal Medicine (1994) 9:339–348.

6. Matthew, "Serotonin 1D (5-HT1D) agonists and other agents in acute migraine" Advances in Headache, (1997) 15(1): 61–81.

7. Pradalier, "Treatment Review: Non-Steroid Anti-Inflammatory Drugs in the Treatment and Long-Term Prevention of Migraine Attacks" Headache (1988) 28:550–557.

8. Pryse-Phillips, "Guidelines for the diagnosis and management of migraine in clinical practice" Can. Med. Assoc. J. (1997) 156(9):1273–1287.

9. Wilkinson, "Migraine and cluster headache—their management with sumatriptan: a critical review of the current clinical experience" Cephalalgia (1995) 15:337–357.

The following paragraphs highlight the present knowledge regarding migraines and their treatment.

Migraine Symptoms and Diagnosis

Migraine is a severe episodic headache characterized by unilateral, intense pulsating headache, nausea, vomiting, sparkling, rainbow-like colors, blank spots in the field of vision, or other auras and sensitivity to light and sounds [Larson, E. David, M.D. Editor-in-Chief. "*Mayo Clinic Family Health Book*" 1994. pp. 502–503]. Migraine refers to a group of symptoms that may occur together. The most noted one is an incapacitating headache, on one side or over the entire head, which can last from 2 to 72 hours. The pain is usually described as throbbing. These headaches are usually, but not always, associated with feeling sick in the stomach or being sensitive to light, sound or movement of the body. The pain is quite severe and often the person with migraine must stay in bed. Dietary, emotional, hormonal and environmental factors may trigger an attack.

In practice there are two types of migraine. The most common is called migraine without aura (Common Migraine) and this accounts for 85% of all sufferers. The second most common type is called migraine with aura (Classical Migraine), which accounts for most of the remaining 15% of sufferers. Aura is a disturbance in the nervous system, which often precedes the headache.

Migraine sufferers sometimes get a warning signal before an attack. Some experience "aura," a disruption of brain function that occurs twenty to thirty minutes before the attack. This is characterized by visual disturbances like flashing lights and blurred vision or a sensation in the body of pins and needles affecting one limb or one side. These disturbances are usually short-lived and almost invariably pass away leaving no long-lasting effects. Other migraine sufferers experience a "prodrome", which occurs several hours or even a day before an attack is initiated. The symptoms may include yawning, fatigue, mood changes, food cravings, and sensitivity to light (photophobia), sound (phonophobia), touch and/or odors. In most of those who have a prodrome, the pattern and headache location remains the same with each migraine attack. Other common symptoms include numbness or a tingling feeling around the lips or hands, hallucinations, loss of speech, symptoms of depression, irritability (some people seek seclusion in a dark room), restlessness, nausea, or loss of appetite, which occur in about 20% of the migraine sufferers. Similar percentages of migraine sufferers lose vision in a specific area (called a blind spot or scotoma) or see jagged, shimmering, or flashing lights. Less commonly, images are distorted; for instance, objects appear smaller or larger than they are.

Migraine is a chronic disorder without cure. No laboratory test is available to help diagnose migraines, but usually the headaches' distinct pattern makes them easy to identify. The headaches are not life-threatening, and there is no proof that they lead to other disorders [Larson, E. David M.D. Editor-in-Chief. "*Mayo Clinic Family Health Book*" 1994. p. 503]. The public health significance of migraine is often overlooked, probably because of its episodic nature and the lack of mortality attributed to disorder. Migraine is, however, often incapacitating, with considerable impact on social activities and work.

Prevalence

The prevalence of migraine is relatively high and said to be approximately 6% of the male population and 18% of the female population. The female preponderance of migraine appears after puberty; in many patients, migraine occurs at the time of menses and improves during pregnancy. It is estimated that only in the US, about 35 million people suffer from migraine. Episodes of migraines can occur weekly in some people; others may have less than one a year [Griffith, H. Winter, M.D. "*All-New Third Edition Complete Guide to Symptoms, Illness & Surgery*" July 1995. p. 425].

Current treatment of migraine

There are several recognized migraine therapeutic drugs. Treatment for many patients having the occasional migraine usually involves simple analgesics (usually in combination with an antiemetic, but such treatments are of limited value), non-steroidal anti-inflammatory agents, or specific agents such as ergotamines or triptans. While no more than sporadically effective, the conventional art recognized that anti-migraine drugs are thought to initially relieve migraine predominantly by causing vasoconstriction. Unfortunately, this conventional art recognized that migraine drugs are associated with significant negative side effects that are linked to excessive vasoactivity in regions of the body not involved in the pathogenesis of migraine. This remote vasoactivity is an effect without any therapeutic benefit to the treatment of migraine. These vasoactive drugs are, in fact, contraindicated in patients with coexisting cardiovascular diseases, or the risk of cardiovascular diseases, such as hypertension, coronary artery disease, or peripheral vascular diseases. Other reported significant side effects are chest pain or pressure, flushing, generalized tingling sensations, nausea, vomiting, pain in the legs and arms, asthenia, drowsiness, and dizziness. Preventative agents such as beta-blockers, tricyclic antidepressants and sodium valproate can reduce but not eliminate migraine attacks in some patients. In the remaining population of migraine sufferers, and in those with intolerable side effects from available drugs, there is a lack of conventional pharmaceutical preparations that exhibit therapeutic effect, without severe side effects. Thus, there remains a great need for migraine specific medications.

OTC analgesics: In some forms of migraine, certain patients have found total or partial relief with the use of non-prescription analgesics such as acetaminophen, aspirin, ibuprofen, and other non-steroidal anti-inflammatory agents, including naproxen and naproxen sodium. However, these agents, when taken alone, are rarely effective in providing complete and rapid alleviation of all the symptoms of migraine, especially when the symptoms of the attack already include nausea or vomiting. Moreover, their onset of action is slow such that relief sometimes does not occur for at least several hours.

Ergotamine Drugs: One of the common treatments for migraine is the administration of compounds having vasoconstrictor properties such as ergotamines or ergotamine-like agents. However, ergotamine is a non-selective vasoconstrictor, which constricts blood vessels throughout the body and has undesirable and potentially dangerous side effects. Ergotamines should not be used by patients with peripheral vascular disease, coronary heart disease, hypertension, impaired hepatic or renal function, severe pruritis or sepsis. It is also contraindicated in women who are, or may become, pregnant. Nausea and vomiting have been reported in up to 10% of patients receiving therapeutic doses of ergotamine. Acute ergotism is a particularly pernicious side effect of ergot drugs, and is characterized by severe central and peripheral vasoconstriction, sometimes resulting in amputation of the affected limbs and/or digits, nausea, vomiting, diarrhea, colic, headache, vertigo, paresthesia, and possibly convulsive seizures. Chronic ergotism is characterized by intermittent claudication, muscle pains, numbness, and cold extremities as well as other gastrointestinal and central nervous system (CNS) side effects. There are treatments, which involve the administration of high dosage of caffeine with ergots or other pharmacological agents. Moreover, ergots and caffeine are potentially addictive with well document withdrawal symptoms.

Triptan drugs (serotonin agonists): Another treatment is the administration of newer therapeutic agents known as serotonin agonists or 5-hydroxy tryptamine (5-HT) agonists. The first of this family, sumatriptan, was undoubtedly, a significant advance in migraine therapy. Sumatriptan succinate sold under the trademark IMITREX by Glaxo Wellcome Inc. Despite sumatriptan utility in migraine treatment it has certain limitations; for example low oral bioavailability, high headache recurrence and contraindication in patients with coronary artery disease.

The main mechanism of action of triptans in migraine is to constrict dilated cranial extracerebral blood vessels. In addition, the triptans can reduce neuropeptide release and plasma protein extravasation across dural vessels and inhibit impulse transmission centrally within trigeminovascular system.

In general, management of migraine is complicated by the lack of a single therapy, which is effective in all patients with the same migraine type and by the need to select either an abortive or prophylactic method of treatment for these migraines. Further complications involve the current use of drugs that cause dependence with extended use, such as the ergot alkaloid ergotamine. Another important consideration is that the more effective anti migraine agents in current use, e.g., the ergots, methysergide, produce severe use-limiting side effects with long term usage.

There is thus a need for an effective drug for alleviating or treating migraine symptoms, which can be used either, before the attack, e.g., at the aura phase, or during the attack, so as to rapidly alleviate symptoms of migraine during a migraine attack and which is devoid of side effects.

Anti-Emetic Drugs

A particularly important application for anti-emetic agents is in the prevention and treatment of nausea and vomiting associated with cancer chemotherapy. Emesis is a well-known and frequent side-effect of cancer chemotherapeutic agents, such as cisplatin. It causes serious problems in cancer chemotherapy, and in some patients emesis is so severe that therapy must be discontinued. Anti-emetic agents are therefore often administered in order to alleviate this side-effect of the cancer chemotherapeutic agent. The anti-emetic agents employed are usually benzamide derivatives, such as metoclopramide, which have dopamine antagonist activity. In view of their dopamine antagonist activity benzamide derivatives such as metoclopramide themselves exhibit serious and undesirable side-effects, such as extrapyramidal effects, i.e. tardive dyskinesia, acute distonia, akathisia and tremor. Physiologically acceptable salts of the carbazolones are described in the U.S. Pat. No. 5,578,628 as potent anti-emetics, which are selective antagonists of 5-hydroxytryptamine (5-HT) at neuronal 5-HT receptors of the type located on terminals of primary afferent nerves, and which are also believed to be present in the central nervous system.

There is thus a need for a safe and effective anti-emetic agent and gastric mobility stimulant, while devoid of undesirable side effects of known anti-emetics which elicit their action via various CNS receptors.

U.S. Pat. No. 6,160,008 discloses the use of S-alkylisothiouronium derivatives, including several novel compounds, as medicaments for increasing arterial blood pressure or for protecting subjects against hyperoxia. These compounds are suggested for the treatment of acute hypotension, e.g., shock conditions and chronic arterial hypotension or oxygen poisoning. The invention is exemplified by the hypertensive effect of S-ethylisothiouronium diethylphosphate under various conditions. However, U.S. Pat. No. 6,160,008 neither teaches nor suggests the use of S-alkylisothiouronium derivatives for treating headache, migraine, or nausea and vomiting.

SUMMARY OF THE INVENTION

Unexpectedly it is now disclosed that S-alkylisothiouronium salt derivatives that were known as hypertensive agents, are also highly efficient in alleviating headache in general and symptoms of migraine, in particular. While reducing the present invention to practice it was also found that these S-alkylisothiouronium salt derivatives were effective in treating nausea and emesis. Subjects with migraine were successfully treated with unexpectedly lower doses of S-ethylisothiouronium diethylphosphate, than required for anti-hypotensive applications. Treatment initiated at the peak of the migraine attack, consistently showed relief within 60 minutes following the drug administration. In some cases dramatic improvement was reported within about 15 minutes.

Thus, according to one aspect of the present invention there is provided a pharmaceutical composition for treatment of headache, migraine, nausea or emesis comprising, as an active ingredient, a compound having the general formula I:

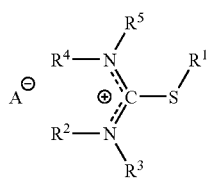

Formula (I)

wherein, $R_1$ is a linear or branched, saturated or unsaturated alkylene, comprising one to eight carbon atoms, optionally substituted with one or more substituent selected from the group consisting of halogen, primary, secondary or tertiary amine, primary, secondary or tertiary alcohol, or interrupted by one or more heteroatom selected from the group consisting of O, N, and S;

$R_2$, $R_3$, $R_4$ and $R_5$ are each independently a hydrogen, hydroxy, linear or branched lower alkyl, linear or branched lower alkenyl, linear or branched lower alkynyl, lower alkoxy, alkoxyalkyl, cycloalkyl, cycloalkylalkyl, lower thioalkoxy, nitro, amino, cyano, sulfonyl, haloalkyl, carboaryloxy, carboalkylaryloxy, alkyl sulfoxide, aryl sulfoxide, alkyl sulfone, aryl sulfone, alkyl sulfate, aryl sulfate, sulfonamide, thioalkyl, optionally substituted by halogen;

$A^-$ is a physiologically acceptable anion;

together with and a pharmaceutically acceptable carrier or diluent.

According to currently preferred embodiments of the invention described below, the physiologically acceptable anion is an anion derived from a phosphorus containing acid, more preferably the group consisting of an anion derived from a phosphorus acid ester, or amide, most preferably the anion is derived from a mono or di-alkyl ester of a phosphorous containing acid.

According to yet another aspect of the present invention there is provided a method of treating a subject suffering from headache, migraine, or nausea the method comprising the step of administering pharmaceutical composition comprising a therapeutically effective amount of a compound having the general formula (I):

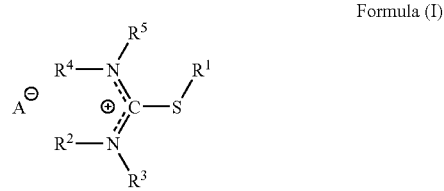

Formula (I)

wherein, $R_1$ is a linear or branched saturated or unsaturated alkylene, comprising one to eight carbon atoms optionally substituted with one or more substituent selected from the group consisting of halogen, primary, secondary or tertiary amine, primary, secondary or tertiary alcohol, or interrupted by one or more heteroatom selected from the group consisting of O, N, and S;

$R_2$, $R_3$, $R_4$ and $R_5$ are each independently a hydrogen, hydroxy, linear or branched lower alkyl, linear or branched lower alkenyl, linear or branched lower alkynyl, lower alkoxy, alkoxyalkyl, cycloalkyl, cycloalkylalkyl, lower thioalkoxy, nitro, amino, cyano, sulfonyl, haloalkyl, carboaryloxy, carboalkylaryloxy, alkyl sulfoxide, aryl sulfoxide, alkyl sulfone, aryl sulfone, alkyl sulfate, aryl sulfate, sulfonamide, thioalkyl, optionally substituted by halogen;

$A^-$ is a physiologically acceptable anion.

According to another aspect of the present invention there is provided a method of preparing a medicament, for headache, migraine or nausea, the method comprising the step of mixing, as an active ingredient, a compound having the general formula (I):

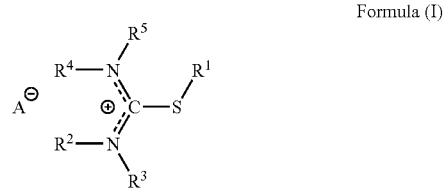

Formula (I)

wherein,

R₁ is a linear or branched saturated or unsaturated alkylene, comprising one to eight carbon atoms optionally substituted with one or more substituent selected from the group consisting of halogen, primary, secondary or tertiary amine, primary, secondary or tertiary alcohol, or interrupted by one or more heteroatom selected from the group consisting of O, N, and S;

R₂, R₃, R₄ and R₅ are each independently a hydrogen, hydroxy, linear or branched lower alkyl, linear or branched lower alkenyl, linear or branched lower alkynyl, lower alkoxy, alkoxyalkyl, cycloalkyl, cycloalkylalkyl, lower thioalkoxy, nitro, amino, cyano, sulfonyl, haloalkyl, carboaryloxy, carboalkylaryloxy, alkyl sulfoxide, aryl sulfoxide, alkyl sulfone, aryl sulfone, alkyl sulfate, aryl sulfate, sulfonamide, thioalkyl, optionally substituted by halogen;

A⁻ is a physiologically acceptable anion;

together with and a pharmaceutically acceptable carrier or diluent.

According to further features in preferred embodiments of the invention, the physiologically acceptable anion is selected from the group consisting of an anion derived from a phosphorus containing acid, a phosphorous acid ester, a phosphorous acid amide, acetate, adipate, alginate, citrate, aspartate, benzoate, benzenesulfonate, bitartarate, bisulfate, butyrate, camphorate, camphorsulfonate, digluconate, glycerophosphate, hemisulfate, heptanoate, hexanoate, fumarate, 2-hydroxyethanesulfonate, isothionate, lactate, maleate, methanesulfonate, nicotinate, 2-naphthalenesulfonate, oxalate, palmoate, pectinate, 3-phenylpropionate, pivalate, propionate, succinate, tartrate, thiocyanate, glutamate, bicarbonate, p-toluenesulfonate, chloride, bromide, iodide and undecanoate.

According to currently preferred embodiments of the invention described below, the physiologically acceptable anion is an anion derived from a phosphorus containing acid, more preferably the group consisting of an anion derived from a phosphorous acid ester or amide, most preferably the anion is derived from a mono or di-alkyl ester of a phosphorous containing acid.

According to still further features in the preferred described embodiments, the medicament is packed and is identified as having anti-headache, anti-migraine or anti-emetic activity.

According to still further features in the described preferred embodiments the compound is selected from the group consisting of:

S-methylisothiouronium methylphosphite;
S-methylisothiouronium dimethylphosphate;
S-ethylisothiouronium metaphosphate;
S-ethylisothiouronium ethylphosphite;
S-ethylisothiouronium diethylphosphate;
S-propylisothiouronium propylphosphite;
S-isopropylisothiouronium metaphosphate;
S-isopropylisothiouronium isopropylphosphite;
S-butylisothiouronium dibutylphosphate; and
S-isobutylisothiouronium isobutylphosphite.

According to still further features in the described preferred embodiments the anti-headache, anti-migraine, anti-nausea or anti-emetic medicament is formulated for oral, or parenteral modes of administration. Among the parenteral routes of administration particularly preferred formulations are suitable for injection, sublingual, transdermal, transmucosal or inhalable administration.

According to still further features in the described preferred embodiments the anti-migraine medicament is formulated as tablets or capsules.

According to still further features in the described preferred embodiments each of the tablets or capsules includes between 10 and 300 mg of the compound.

According to still further features in the described preferred embodiments each of the tablets or capsules includes between 20 and 200 mg of the compound.

According to still further features in the described preferred embodiments each of the tablets or capsules includes between 30 and 80 mg of the compound.

According to still further features in the described preferred embodiments, the method further comprising the steps of packaging the medicament and identifying the medicament as having anti-headache, anti-migraine, anti-nausea or anti-emetic activity.

According to preferred embodiments the therapeutically effective amount ranges between 0.1 and 3 mg/kg body weight.

According to further preferred embodiments the therapeutically effective amount ranges between 0.4 and 1.6 mg/kg body weight.

According to currently most preferred embodiments the therapeutically effective amount ranges between 0.5 and 1.2 mg/kg body weight.

According to still further features in the described preferred embodiments the therapeutically effective amount is selected such that in less than 60 minutes following administration a substantial relief in migraine symptoms is experienced.

According to certain preferred embodiments the compound is administered following onset of symptoms of a headache, in particular a migraine, or nausea.

According to additional preferred embodiments the compound is administered upon onset of a headache, particularly a migraine, or nausea.

It is understood that the while migraine is the most severe form of headache, the methods of treatment of the present invention are suitable also for other types of headaches and nausea, including but not limited to PMS or hangover associated headaches and nausea. This is particularly appropriate due to the negligible side effects observed in human subjects with the compositions and methods of the present invention.

Compounds of formula (I) inhibit emesis. The compounds are therefore also of use as anti-emetic agents, i.e. in the prevention and treatment of nausea and vomiting. The compounds are especially valuable for the prevention of emesis induced by cancer chemotherapeutic agents such as cisplatin. Particular mention may also be made of the treatment of radiation-induced emesis. Thus, the compounds of formula (I) may be used in the prevention of emesis induced by radiation therapy, e.g. irradiation of the thorax or abdomen, such as in the treatment of cancer; or in the treatment of radiation sickness. It will be appreciated that the compounds of formula (I) may be used prophylactically and references in this specification to treatment include prophylactic treatment as well as the alleviation of acute symptoms.

According to still further features in the described preferred embodiments the step of administering the compound is effected at or prior to onset of nausea. It will be appreciated by the skilled artisan that oral administration may be less desirable after onset of nausea.

The present invention successfully addresses the shortcomings of the presently known medications by providing an efficient compound for treating and/or alleviating the symptoms of headache, in particular migraine, or nausea. The currently preferred compound had no apparent side effects, was shown to be potent in low doses and to elicit a therapeutic/relieving effect within a short time period as compared to currently marketed drugs.

DESCRIPTION OF THE PREFERRED EMBODIMENTS

The present invention relates to the use S-alkylisothiouronium derivatives for the treatment of headache, in particular migraine, or nausea and vomiting. The compositions of the invention are effective in preventing or alleviating emesis associated with migraine or other medical conditions such as chemotherapy or radiotherapy, as well as other symptoms of migraine including phonophobia and photophobia. These compounds were known before to affect arterial blood pressure in cases of acute hypotension (e.g., following hemorrhage, trauma, shock or poisoning).

Before explaining at least one embodiment of the invention in detail, it is to be understood that the invention is not limited in its application to the details set forth in the following description or exemplified in the Examples section. The invention is capable of other embodiments or of being practiced or carried out in various ways. Also, it is to be understood that the phraseology and terminology employed herein is for the purpose of description and should not be regarded as limiting.

As used herein, the term "migraine" is understood expansively to include a subset of headache characterized by unusual severity, unilateral, throbbing, headache pain persisting for 4–72 hours and can include also one or more of the following symptoms: nausea, vomiting, sensitivity to light and/or sounds with or without a preceding "aura" and visual photophobia (e.g., visual disturbances).

According to one aspect of the present invention there is provided an anti-headache, anti-migraine, anti-nausea or anti-emesis medicament comprising, as an active ingredient, a compound having the general formula (I):

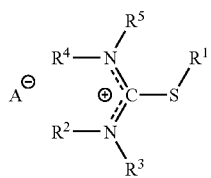

wherein, $R_1$ is a linear or branched saturated or unsaturated alkylene, comprising one to eight carbon atoms optionally substituted with one or more substituent selected from the group consisting of halogen, primary or secondary amine, primary or secondary alcohol, or interrupted by one or more heteroatom selected from the group consisting of O, N, and S;

$R_2$, $R_3$, $R_4$ and $R_5$ are each independently a hydrogen, hydroxy, linear or branched lower alkyl, linear or branched lower alkenyl, linear or branched lower alkynyl, lower alkoxy, alkoxyalkyl, cycloalkyl, cycloalkylalkyl, lower thioalkoxy, nitro, amino, cyano, sulfonyl, haloalkyl, carboaryloxy, carboalkylaryloxy, alkyl sulfoxide, aryl sulfoxide, alkyl sulfone, aryl sulfone, alkyl sulfate, aryl sulfate, sulfonamide, thioalkyl, optionally substituted by halogen;

$A^-$ is a physiologically acceptable anion;

together with and a pharmaceutically acceptable carrier or diluent.

Preferably, the physiologically acceptable anion is derived, without limitation, from a phosphorus containing acid, the group consisting of an anion derived from a phosphorus containing acid, acetate, adipate, alginate, citrate, aspartate, benzoate, benzenesulfonate, bitartarate, bisulfate, butyrate, camphorate, camphorsulfonate, digluconate, glycerophosphate, hemisulfate, heptanoate, hexanoate, fumarate, hydrochloride, 2-hydroxyethanesulfonate, isothionate, lactate, maleate, methanesulfonate, nicotinate, 2-naphthalenesulfonate, oxalate, palmoate, pectinate, 3-phenylpropionate, pivalate, propionate, succinate, tartrate, thiocyanate, phosphate, glutamate, bicarbonate, p-toluenesulfonate, chloride, bromide, iodide and undecanoate.

According to currently preferred embodiments of the invention described below, the physiologically acceptable anion is an anion derived from a phosphorus containing acid, more preferably the group consisting of an anion derived from a phosphorus acid ester or amide, most preferably the anion is derived from a mono or di-alkyl ester of a phosphorous containing acid.

As used herein and in the claims, the term "alkylene" refers to a saturated or unsaturated hydrocarbon chain including straight chain or branched chain alkyl, alkenyl or alkynyl.

As used herein, the term "alkyl" refers to a saturated hydrocarbon chain containing 1 to 30, preferably 1 to 6 carbon atoms, such as, but not limited to, methyl, ethyl, n-propyl, isopropyl, n-butyl, isobutyl, tert-butyl, n-pentyl, n-hexyl, and the like. As used herein the term alkyl also reads on haloalkyls, which contain halogen atoms. Alkyl also includes heteroalkyl with heteroatoms of sulfur, oxygen and nitrogen.

"Alkenyl" and "alkynyl" are used to mean straight or branched chain hydrocarbon groups having from 2 to 12 carbons and unsaturated by a double or triple bond respectively, such as vinyl, allyl, propargyl, 1-methylvinyl, but-1-enyl, but-2-enyl, but-2-ynyl, 1 methylbut-2-enyl, pent-1-enyl, pent-3-enyl, 3-methylbut-1-ynyl, 1,1-dimethylallyl, hex-2-enyl and 1-methyl-1-ethylallyl;

The term "cycloalkyl" is used herein to mean cyclic radicals, including but not limited to, cyclopropyl, cyclopentyl, cyclohexyl, and the like.

The term "cycloalkylalkyl" as used herein refers to a cycloalkyl group appended to a lower alkyl radical, including, but not limited to cyclohexylmethyl.

The "alkoxyalkyl" mentioned for R substitutes is preferably a group containing a total of 1–22 carbon atoms. As example, methoxyethyl, methoxypropyl, methoxybutyl, ethoxyethyl, ethoxypropyl, ethoxybutyl, n-propoxyethyl, and iso-propoxyethyl, can be mentioned.

The term "alkoxy" as used herein refers to an alkyl group attached to the parent molecular group through an oxygen atom.

The term "alkoxyalkoxy" as used herein refers to an alkoxy group attached to the parent molecular group through an alkoxy group.

The term "halo" or "halogen" as used herein refers to I, Br, Cl or F.

The term "carboxy" as used herein refers to the radical —COOH. The term "ester" refers to —COOR; and the term "amide" refers to —CONH$_2$ or —CONHR or —CONR$_2$. The term "cyano" as used herein refers to the radical —CN.

Phosphorus containing and other salts of S-alkylisothiouronium synthesized in a variety of ways, which are well known in the art, for example by alkylating thiourea with appropriate trialkylphosphates or dialkylphosphites while heating in an organic solvent.

Without excluding other options, which are listed below, presently S-ethylisothiouronium diethylphosphate is the preferred compound for the treatment of headache, in particular migraine, and nausea or vomiting. Other examples of S-alkylisothiouronium derivatives which can be used to treat migraine according to the present invention include, but are not limited to, S-methylisothiouronium methylphosphite; S-methylisothiouronium dimethylphosphate; S-ethylisothiouronium metaphosphate; S-ethylisothiouronium ethylphosphite; S-ethylisothiouronium diethylphosphate; S-propylisothiouronium propylphosphite; S-isopropylisothiouronium metaphosphate; S-isopropylisothiouronium isopropylphosphite; S-butylisothiouronium dibutylphosphate; and S-isobutylisothiouronium isobutylphosphite.

These compounds are known to be safe for human use as it is well known in the art that phosphorus containing derivatives of S-alkylisothiouronium have a low toxicity and their $LD_{50}$ (lethal dose 50%) is in the range of 100–1000 mg/kg, which is far above the therapeutic doses of these compounds.

The anti-headache, anti-migraine, anti-nausea or anti-emetic medicament of the present invention is preferably packed and is preferably identified as having such activity. Such identification can be printed, for example, on a package insert with the medicament or on a package or container which contains the medicament.

A compound according to the present invention can be administered to a treated subject per se, or in a pharmaceutical composition where it is mixed with suitable carriers or excipients.

As used herein a "pharmaceutical composition" refers to a preparation of one or more of the compounds described herein, or physiologically acceptable salts or prodrugs thereof, with other chemical components such as physiologically suitable carriers and excipients. The purpose of a pharmaceutical composition is to facilitate administration of a compound to an organism.

The term "prodrug" refers to an agent, which is converted into an active parent drug in vivo. Prodrugs are often useful because in some instances they may be easier to administer than the parent drug. They may, for instance, be bioavailable by oral administration whereas the parent drug is not. The prodrug may also have improved solubility compared to the parent drug in pharmaceutical compositions.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Pharmaceutical compositions may also include one or more additional active ingredients, such as, but not limited to, conventional anti-migraine agents.

Pharmaceutical compositions of the present invention may be manufactured by processes well known in the art, e.g., by means of conventional mixing, dissolving, granulating, grinding, pulverizing, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active compounds into preparations which, can be used pharmaceutically. Proper formulation is dependent upon the route of administration chosen.

For injection, the compounds of the invention may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants for example DMSO, or polyethylene glycol are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by inhalation, the compounds for use according to the present invention are conveniently delivered in the form of an aerosol spray presentation from a pressurized pack or a nebulizer with the use of a suitable propellant, e.g., dichlorodifluoromethane, trichlorofluoromethane, dichlorotetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Pharmaceutical compositions for parenteral administration include aqueous solutions of the active preparation in water-soluble form. Additionally, suspensions of the active compounds may be prepared as appropriate oily injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the compounds, to allow for the preparation of highly concentrated solutions.

Alternatively, the active ingredient may be in powder form for constitution with a suitable vehicle, e.g., sterile, pyrogen-free water, before use.

The compounds of the present invention may also be formulated in rectal compositions such as suppositories or retention enemas, using, e.g., conventional suppository bases such as cocoa butter or other glycerides.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

Pharmaceutical compositions suitable for use in context of the present invention include compositions wherein the active ingredients are contained in an amount effective to achieve the intended purpose. More specifically, a therapeutically effective amount means an amount of a compound effective to prevent, alleviate or ameliorate symptoms of a disease of the subject being treated.

Determination of a therapeutically effective amount is well within the capability of those skilled in the art, especially in light of the detailed disclosure provided herein.

Toxicity and therapeutic efficacy of the compounds described herein can be determined by standard pharmaceutical procedures in cell cultures or experimental animals, e.g., by determining the $IC_{50}$ (the concentration which provides 50% inhibition) and the $LD_{50}$ (lethal dose causing death in 50% of the tested animals) for a subject compound. The data obtained from these cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p.1).

Depending on the severity and responsiveness of the condition to be treated, dosing can also be a single administration of a slow release composition, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Sustained release tablets or capsules which contain S-alkylisothiouronium may be used either before the attack, e.g., in persons about to undergo chemotherapy or other treatments that are known to engender nausea or vomiting, in women who are aware that their premenstrual period is typically followed by nausea or a migraine, or in those migraine patients who experience "aura" and can identify this as a pre-migraine stage. Also, the tablet or the capsule can be formulated in a way that a portions of the active ingredient is released immediately, to provide an initial migraine alleviation, whereas the other portion is released slowly and in measured quantities.

As used herein, the term, "initial migraine alleviation" refers to the reduction or abolition of migraine symptoms within a predetermined time range, post administration and particularly in the present invention, within about 10–60 minutes post administration.

Each of the tablets or capsules of the present invention preferably contains between 10 and 300 mg, preferably 20 and 200 mg, more preferably between 30 and 80 mg of the active compound (S-alkylisothiouronium derivatives). As used herein the term "about" refers to ±20%.

According to another aspect of the present invention there is provided a method of preparing an anti-headache, anti-migraine, anti-nausea or anti-emesis medicament. The method according to this aspect of the present invention is effected by mixing, as an active ingredient, a compound having the general formula (I):

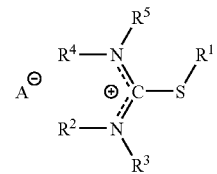

wherein $R_1$ is a linear or branched saturated or unsaturated alkylene, comprising one to eight carbon atoms optionally substituted with one or more substituent selected from the group consisting of halogen, primary or secondary amine, primary or secondary alcohol, or interrupted by one or more heteroatom selected from the group consisting of O, N, and S;

$R_2$, $R_3$, $R_4$ and $R_5$ are each independently a hydrogen, hydroxy, linear or branched lower alkyl, linear or branched lower alkenyl, linear or branched lower alkynyl, lower alkoxy, alkoxyalkyl, cycloalkyl, cycloalkylalkyl, lower thioalkoxy, nitro, amino, cyano, sulfonyl, haloalkyl, carboaryloxy, carboalkylaryloxy, alkyl sulfoxide, aryl sulfoxide, alkyl sulfone, aryl sulfone, alkyl sulfate, aryl sulfate, sulfonamide, thioalkyl, optionally substituted by halogen;

$A^-$ is a physiologically acceptable anion;

together with and a pharmaceutically acceptable carrier or diluent.

According to a preferred embodiment of the present invention, the method further includes the step of packaging the medicament and identifying the medicament as having anti-headache, anti-migraine, anti-nausea or anti-emetic activity as is further described above. The identification of the medicament as an anti-headache, in particular an anti-migraine agent or as an anti-emetic agent are novel indications for S-alkylisothiouronium derivatives, which are known as hypertensive agents and were not indicated before for the purposes of treating or alleviating the symptoms of headache, migraine or nausea.

In still another aspect of the present invention there is provided a method of treating headache, migraine, or nausea The method according to this aspect of the present invention is effected by administering to a subject a therapeutically effective amount of a compound having the general formula (I):

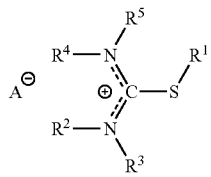

wherein
R₁ is a linear or branched saturated or unsaturated alkylene, comprising one to eight carbon atoms optionally substituted with one or more substituent selected from the group consisting of halogen, primary or secondary amine, primary or secondary alcohol, or interrupted by one or more heteroatom selected from the group consisting of O, N, and S;

R₂, R₃, R₄ and R₅ are each independently a hydrogen, hydroxy, linear or branched lower alkyl, linear or branched lower alkenyl, linear or branched lower alkynyl, lower alkoxy, alkoxyalkyl, cycloalkyl, cycloalkylalkyl, lower thioalkoxy, nitro, amino, cyano, sulfonyl, haloalkyl, carboaryloxy, carboalkylaryloxy, alkyl sulfoxide, aryl sulfoxide, alkyl sulfone, aryl sulfone, alkyl sulfate, aryl sulfate, sulfonamide, thioalkyl, optionally substituted by halogen;

A⁻ is a physiologically acceptable anion;

together with and a pharmaceutically acceptable carrier or diluent.

It should be noted in this respect that in a ongoing clinical trials, which is described in detail in the Examples section that follows, human subjects were assessed for their response and for the beneficial effect S-ethylisothiouronium diethylphosphate. Unexpectedly, these subjects showed a dramatic, beneficial effect of the drug, which was administered during the migraine attack. The administered dose was substantially lower than the effective oral dose which is used for treating hypotension (which is generally about 100 mg). Moreover, the drug was found to be potent in reducing the migraine symptoms within a relatively short period of time, around 45 minutes on average, while the subject was at the peak of the migraine attack.

Apart from eliminating the acute headache, the drug also eliminated the unpleasant sensation of nausea, photophobia, and improved the impaired sight focusing. The drug was shown to have a fast and prolonged effect. In addition, the rapid mode of action suggests of fast absorption of the drug. In addition, no side effects were apparent.

These results are extremely unexpected. It will be appreciated in this respect that recognized migraine drugs act most quickly when administered by the parenteral route. Also, no matter how administered, therapeutic relief of migraine is often not obtained using these recognized migraine drugs. When administered orally, the recognized migraine drugs act significantly more slowly than when parenterally administered, such that pain relief, when achieved, may not be apparent for up to 2–3 hours post-administration.

As used herein the term "therapeutically effective amount" or "therapeutically efficient" as to a drug dosage, refer to dosage that provides the specific pharmacological response for which the drug is administered in a significant number of subjects in need of such treatment. The "therapeutically effective amount" may vary according, for example, the physical condition of the patient, the age of the patient and the severity of the disease. It is emphasized that migraine headache is not well understood and the etiology of particular migraines vary, as does the response to particular drugs. Thus, reference to "specific pharmacological response for which the drug is administered in a significant number of subjects in need of such treatment" is a recognition that a "therapeutically effective amount", administered to a particular subject in a particular instance will not always abort migraine onset or relieve an actual migraine headache, even though such dosage is deemed a "therapeutically effective amount" by those skilled in the art.

The term "prolonged effect" in relation to S-ethylisothiouronium diethylphosphate relates to its pharmacokinetic half-life. It should be noted in this respect that in the case reports described in the Examples section that follows, the migraine attack was eliminated within minutes post administration of the drug, and in the reported cases no additional treatment was required.

The preliminary clinical trial revealed another two important issues that relate to the "relapse" of the headache and to the side effects of the currently marketed anti-migraine drugs, some hours after the administration. Headache recurrence after successful initial treatment is another weakness of some currently available anti-migraine preparations. That is, after a dosage of a known therapeutic agent has been administered to a subject in an effective amount to initially treat a migraine attack, and migraine alleviation has been observed, migraine symptoms occur again from as soon as about 1–8 hours after first relief to about 12 to 24 hours later. The headache, which occurs under the circumstances described above has been variously and interchangeably termed a "rebound," "relapse," "recurrent," "follow on," or "secondary" headache. The terms not withstanding, it is presently unknown as to whether this later headache is a continuation of the physiological chain of events that caused original headache, or a new headache due to other or repeated, but unrelated, underlying pathology. It is also possible that the follow on headache is a response to therapeutic agents, which initially were successful in treating the initial migraine symptoms. The terms "rebound," "relapse," "recurrent" "follow on," and "secondary" (as defined below) are considered synonymous as used herein without inferring a mechanism or cause of migraine headache.

According to the described case reports, this phenomenon was not observed while receiving S-ethylisothiouronium diethylphosphate.

It should be noted in this respect that migraine attacks are associated with dilation of blood vessels in the head, and relief of a migraine headache is associated inter alia with the reduction of such vasodilatation. As a side effect, anti migraine agents can cause abnormal blood flow (by either vasodilatation or vasoconstriction). Thus, the striking therapeutic effect of S-ethylisothiouronium diethylphosphate as an anti-migraine agent together with its known potency in controlling abnormal blood vessel flow is the answer for the debilitating effects of migraine symptoms without the side effects of known anti migraine agents.

In addition, S-ethylisothiouronium diethylphosphate, can be beneficially combined with another anti-migraine agent such as an ergotamine derivative, or a serotonergic agonist. The combined treatment will require a lower amount of each drug while the addition of S-ethylisothiouronium diethylphosphate to a known therapeutic agents will reduce side effects of the known drugs and will provide initial relief to the sufferers within minutes.

As was discussed before the compound is formulated for oral, injectable, inhalable or transdermal administration.

Oral administration is by tablets or capsules, wherein the preferred dose is ranging between 10 and 200 mg of the compound, preferably, between 20 and 70 mg of the compound and according the clinical results is about 50 mg of the compound. Thus, the therapeutically effective amount of the compound ranges between 0.1 and 3.0 mg/kg body weight, preferably between 0.4 and 1.6 mg/kg body weight, more preferably from 0.5 and 1.2 mg/kg body weight.

The above ranges of therapeutic effective doses are selected so as to exert a substantial relief in migraine symptoms within 15–60 minutes post administration.

In a preferred embodiment of the present invention the administration of an S-alkylisothiouronium derivative is effected at or following the onset of a migraine.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions illustrate the invention in a non-limiting fashion.

Example 1

Results of the Clinical Trials in Treatment of Migraine Attack by Difetur Oral Formulation (Tablets)

Study Protocol

Dose escalating exploratory study on the safety and efficacy of Difetur tablets for the treatment of acute migraine attack.

1. Study Objective

The purpose of following exploratory protocol is to evaluate the safety and potential efficacy of Difetur (S-ethylisothiouronium diethylphosphate) tablets, in escalating doses starting at 10 mg and up to 50 mg, in the treatment of a single acute migraine attack. The study was designed as an open study in a selected population of subjects classified according to IHS criteria as suffering from migraine headaches of moderate or severe intensity, without aura. The study was conducted according to established international criteria for evaluating safety and efficacy for migraine treatment.

2. Study Design

The study was performed as a 5 arm (groups) study. Only female patients classified as suffering from migraine without aura, according to IHS criteria are enrolled in the study. Each group consists of ten migraine patients who are treated during an acute migraine attack with Difetur tablets in a hospital setting. The initial dose of Difetur is 10 mg (1 tablet), consequently increasing to 20 mg, 30 mg, 40 mg, and 50 mg. The total number of patients to be enrolled is 50. The patients are hospitalized and followed for at least 4 hours to assess the safety, efficacy and possible side effects of Difetur.

3. Drug Administration

In the first group of 10 patients each receive the initial dose of 10 mg of the study medication in a single tablet form. The dose of 50 mg is given as two tablets of 25 mg each. The tablets are individually packed in blister package, and have a label identifying the study medication as an investigational drug. Each dose in an escalating manner is given to 10 patients. The medication is swallowed with a glass of water under the supervision of an attending physician.

4. Efficacy Evaluation 4.1 Primary Efficacy Objective is Headache Reduction.

Headache severity is graded verbally in a 4-points scale: severe (grade 4), moderate (grade 3), mild (grade 2), or no pain (grade 1). Success is considered as a reduction of the headache severity from a severe or moderate headache (grade 3–4) to mild or no pain (grade 1–2).

4.2 Secondary Efficacy Targets are the Reduction of Nausea, Vomiting and Light and Sound Sensitivity.

These are assigned for their presence, absence or disappearance as documented by the patient.

Study Results.

TABLE 1

Summary of Results in Migraine Headache Treatment (Treatment Initiated During Migraine Attack).

| No. | Dosage[1] (mg) | Percentage of Patients Benefited by Treatment[2] | Time elapsed to Effect[3] (min) |
|---|---|---|---|
| 1 | 10 | 0 | — |
| 2 | 20 | 70 | 43 |
| 3 | 30 | 70 | 58 |

[1]Dosage of Difetur per treatment.
[2]Relief of headache is considered effective if the patient reported a reduction of the headache severity from severe or moderate (grades 3–4) to mild or no pain (grades 1–2). [Headache severity scale: 1 = No pain; 2 = mild; 3 = moderate; 4 = severe pain].
[3]Time after ingestion of drug at which a patient reported headache reduction to grade 1–2.

Unexpectedly, it is now disclosed that the low doses of Difetur, which are ineffective or less effective at alleviating the severity of the migraine headache, are already effective at reducing or abolishing the symptoms of nausea Moreover it was observed that the time elapsed until relief from nausea was reported was shorter than that recorded for reduction of the severity of the headache. This supports the use of the drug as an anti-emetic.

TABLE 2

Summary of Results in Emesis Treatment During Migraine Attack.

| No. | Dosage[4] (mg) | Percentage of Patients Affected by Treatment[5] | Time elapsed until Effect[6] (min) |
|---|---|---|---|
| 1 | 10 | 70 | 28 |
| 2 | 20 | 100 | 25 |
| 3 | 30 | 100 | 29 |

[4]Dosage of Difetur per treatment.
[5]The percent of patients that exhibited a positive anti-emetic response to Difetur administration.
[6]Time after ingestion of drug at which a patient reported termination of emesis.

Example 2

Multiple Doses of Difetur for Relief of Migraine Headache

Case Report 1

Previous medical history: The subject is a smoking, 30 years old female first diagnosed as a classical migraine sufferer at 17 years of age. Except for this she is completely healthy. Until two years ago the frequency of the migraine attacks was seven episodes per month. During the last two years she was treated with different kinds of recognized medications, with little or no success. Due to lack of response to the medical treatment during the migraine attacks, she tried alternative medicine treatments.

As a result of the S-ethylisothiouronium diethylphosphate treatment the frequency of migraine attacks she suffered from, was reduced to about three each month. In addition, the nature of the migraine attacks has changed to become of a weaker strength. The reported effect of the S-ethylisothiouronium diethylphosphate treatment on the migraine pain was that it became significantly weaker. At present, she experiences approximately only two migraine attacks monthly, mostly before the menstruation period, during very hot weather conditions, or when extreme changes in the weather occurs. The pre menstruation-period migraine attacks are usually longer and more acute than the other migraine attacks. The duration of each migraine attack lasts 24–72 hours.

Past medical treatment: The medication that she was treated with, prior to the alternative medicine treatments were: Temigran, Migraleve, Imitrex and Zomig. These treatments were terminated due to various strong side effects, included hand tremor, shivering, dryness of the mouth, nausea and vomiting.

Treatment with S-ethylisothiouronium diethylphosphate:

First attack: The subject suffered an acute migraine attack that lasted 72 hours. Despite her intake of prescription medication every two hours the intensity of the Migraine associates pain did not change. On the next day the subject received a single dose of 50 mg S-ethylisothiouronium diethylphosphate (2 tablets of 25 mg each). The drug was taken on empty stomach; the subject did not eat nor drink anything before swallowing the drug. Between 10 to 15 minutes following administration the pain abruptly disappeared, as did all other symptoms, which appeared during the migraine attack.

Second attack (three weeks later) The second migraine attack started during the night. On the next day the subject received once again 2 tablets of S-ethylisothiouronium diethylphosphate (50 mg). This time the intake of the tablets was during the peak of the migraine attack, after having a meal. Within 20 minutes the headache was relieved, the subject was able to focus her eyesight, and the photophobia disappeared. There was a weak headache but its intensity was reduced. Three hours later the subject took two more tablets of S-ethylisothiouronium diethylphosphate (50 mg). Within 15 minutes the migraine pain disappeared.

Third attack (two and a half weeks after the second attack) the migraine attack started on her way to work. An hour after onset within the peak of the migraine attack, the subject received 2 tablets of S-ethylisothiouronium diethylphosphate (each of 25 mg). Drug was taken on empty stomach. Within 11 minutes the migraine symptoms disappeared.

Side effects: No side effects following the intake of S-ethylisothiouronium diethylphosphate were apparent.

Case Report 2

Previous Medical History: The subject is a non-smoking 34 years old female suffering from migraine attacks during the last two years. The frequency of the migraine attacks is once a month before the menstruation period. The pain appears in the temples, the sinuses and spreads down to the lower jaw. The duration of the photophobia was about 48 hours. So far the subject has not applied to receive specific medical treatment and used to take conventional analgesic drugs.

Past medical Treatment: Conventional pain relief (analgesic) drugs.

Treatment with S-ethylisothiouronium diethylphosphate:

First attack: The onset of an acute migraine attack was in the morning and the symptoms grew stronger during the day. Just before noon time the subject received one tablet of S-ethylisothiouronium diethylphosphate (25 mg). No substantial change in the migraine pain was observed. Two hours later the subject received 2 more tablets of S-ethylisothiouronium diethylphosphate (each of 25 mg). Ten minutes later, the migraine pain disappeared.

Second attack (about four weeks after the first attack) The migraine attack started as a consequence of very hot weather conditions. The intensity of this attack was greater than the usual migraine attacks. In the morning, the subject received 2 tablets of S-ethylisothiouronium diethylphosphate (50 mg) that were taken on an empty stomach. Within 20 minutes of S-ethylisothiouronium diethylphosphate intake there was a significant relief in migraine pain. Fifteen minutes later the pain disappeared. Later that day, during the afternoon, the subject suffered a weak pain. This time the subject self administered analgesic drugs and the pain disappeared.

Side effects: No side effects following the intake of 25 or 50 mg S-ethylisothiouronium diethylphosphate were detected by the monitor.

Discussion of the Results

Both case reports and especially the first case show a dramatic, unexpected, beneficial effect of S-ethylisothiouronium diethylphosphate administered during the migraine attack. The effective dose was about half the effective dose used to treat hypotension (which is about 50–100 mg). Moreover, the drug was found to be highly potent in eliminating the migraine symptoms within less than 20 minutes, while the subject was at the peak of the migraine attack. Apart from eliminating the acute headache, the drug also eliminated nausea and the unpleasant sensation of photophobia, and improved the impaired sight focusing. The striking effects of the drug were repeated three times in the first subject and twice in the second subject. It seems that the drug is more effective when administered on an empty stomach. In addition, no side effects were detected.

Thus, it can be concluded that S-ethylisothiouronium diethylphosphate is a highly potent drug for treating and alleviating migraine symptoms. It has a rapid mode of action, an effective low dose, and according to the described case reports it is devoid of side effects.

Example 3

Anti-Emesis in Test Animals

The effect of the test compounds on emesis is tested in ferrets according to the general method described by Florezyk, Schurig and Bradnet (Cancer Treatment Report, 1982

66(1) 187–9) and summarized below. Both the test compound and cisplatin are prepared and administered in normal saline.

a) Control—Without Test Compound

Emesis is induced in groups of 6 male ferrets weighing between 1.5–2 kg, by intravenous administration of cisplatin at a dose of 10 mg/kg. The onset of emesis occurs between 30 and 75 minutes after injection and over a period of 2 hours the number of vomits/retches (episodes) is in the range 30–60 (average 40 vomits/retches per 2 h). Behavioral changes characteristic of emesis are also noted.

b) With Test Compound

The test compound is administered to groups of 6 male ferrets (1.5–2 kg) by intravenous administration at doses of 0.01, 0.1 and 1 mg/kg, immediately prior to administration of cisplatin as described above. The animals are observed for 3 hours.

The effect of the test compound on emesis is also evaluated following intraperitoneal administration, using a similar procedure to that described above. Thus cisplatin is administered intraperitoneally to a group of male ferrets at a dose of 5–10 mg/kg, and the time to onset of emesis and the number of emetic episodes are recorded. In a second group of male ferrets the test compound is administered at a dose of 1 mg/kg i.p. 30 minutes before and 1 hour after intraperitoneal administration of cisplatin.

Example 4

Clinical Trials in Treatment of Migraine Attack by Intravenous Difetur

1. Study Summary

The purpose of following exploratory protocol was to evaluate the safety and potential efficacy of Difetur 10% solution for injection, in dose 0.6 mg/kg, in treatment of a single acute migraine attack. The study was designed as an open study in a selected population of subjects classified according to IHS criteria as suffering from migraine headaches of moderate or severe intensity, without aura. The study was conducted according to established international criteria for evaluating safety and efficacy for migraine treatment.

2. Drug Administration

Difetur was presented as 10% (100 mg/mL) solution in 1 mL ampoules. It was dissolved in 100 mL of saline solution in intravenous device before treatment. The dose of Difetur was 0.6 mg/kg, given by intravenous drip during 10 min.

3. Efficacy Evaluation

Headache severity was graded verbally on a 5-point scale: very severe (grade 4), severe (grade 3), moderate (grade 2), mild (grade 1), no pain (grade 0). Success was considered as reduction of the headache severity from very severe, severe or moderate (grade 4–2) to mild or no pain (grade 1–0).

4. Study Results.

13 patients with various grades of headache severity were included in the study. Except for one patient in whom no headache reduction was noted, all the rest had significant headache relief. The efficacy and time elapsed to effect are presented in table below:

TABLE 3

Summary of Results in Migraine Headache IV Treatment

| Headache grade | No. of Patients. | Percentaoe of Patients Benefited by Treatment[1] | Mean time elapsed to Effect (min)[2] |
|---|---|---|---|
| 4 | 1 | 100% | 50 |
| 3 | 4 | 100% | 25.5 |
| 2 | 8 | 87% | 13.7 |

[1]Success was considered as reduction of the headache severity from very severe, severe or moderate (grade 4–2) to mild or no pain (grade 1–0).
[2]Time after initiation of treatment after which a patient reported headache reduction to severity grade 1–0.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of treating headache or migraine, the method comprising the step of administering to a subject in need of such treatment a therapeutically effective amount of a composition consisting essentially of (a) a compound selected from the group consisting of S-methylisothiouronium methylphosphite; S-methylisothiouronium dimethylphosphate; S-ethylisothiouronium metaphosphate; S-ethylisothiouronium ethylphosphite; S-ethylisothiouronium diethylphosohate; S-propylisothiourium propylphosphite; S-isopropylisothiouronium metaphosphate; S-isopropylisothiouronium isopropylphosphite; S-butylisothiouronium dibutylphosphate; and S-isobutylisothiouronium isobutylphosphite, and (b) a pharmaceutically acceptable carrier or diluent; wherein the composition is formulated as tablets or capsules.

2. The method of claim 1, wherein each of said tablets or capsules comprises between 10 and 300 mg of the compound.

3. The method of claim 1, wherein each of said tablets or capsules comprises between 20 and 200 mg of the compound.

4. The method of claim 1, wherein each of said tablets or capsules comprises between 30 and 80 mg of the compound.

5. The method of claim 1, wherein said therapeutically effective amount ranges of the compound between 0.1 and 3 mg/kg body weight.

6. The method of claim 1, wherein said therapeutically effective amount ranges of the compound between 0.4 and 1.6 mg/kg body weight.

7. The method of claim 1, wherein said therapeutically effective amount ranges of the compound between 0.5 and 1.2 mg/kg body weight.

8. The method of claim 1, wherein said wherein the compound is S-ethylisothiouronium diethylphosphate.

9. The method of claim 1, wherein said therapeutically effective amount is selected such that less than one hour after administration a substantial relief in migraine symptoms is experienced.

10. The method of claim 1, wherein said step of administering the compound is effected following an onset of a headache or a migraine.

11. The method of claim 1, wherein said step of administering the compound is effected at onset of a headache or a migraine.

12. The method of claim 1, wherein the carrier or diluent comprises a sugar, a starch or cellulose preparation or a physiologically acceptable polymer and optionally includes a disintegrating agent or a salt thereof.

13. A method of alleviating nausea or vomiting, the method comprising the step of administering to a subject suffering from nausea or vomiting a therapeutically effective amount of a composition consisting essentially of (a) a compound selected from the group consisting of S-methylisothiouronium methylphosphite; S-methylisothiouronium dimethylphosphate; S-ethylisothiouronium metaphosphate; S-ethylisothiouronium ethylphosphite; S-ethylisothiouronium diethylphosphate; S-propylisothiouronium propylphosphite; S-isopropylisothiouronium metaphosphate; S-isopropylisothiouronium isopropylphosphite; S-butylisothiouronium dibutylphosphate; and S-isobutylisothiouronium isobutylphosphite, and (b) a pharmaceutically acceptable carrier or diluent; wherein the composition is formulated as tablets or capsules.

14. The method of claim 13, wherein each of said tablets or capsules comprises between 10 and 300 mg of the compound.

15. The method of claim 13, wherein each of said tablets or capsules comprises between 20 and 200 mg of the compound.

16. The method of claim 13, wherein each of said tablets or capsules comprises between 30 and 80 mg of the compound.

17. The method of claim 13, wherein said therapeutically effective amount ranges of the compound between 0.1 and 3 mg/kg body weight.

18. The method of claim 13, wherein said therapeutically effective amount ranges of the compound between 0.4 and 1.6 mg/kg body weight.

19. The method of claim 13, wherein said therapeutically effective amount ranges of the compound between 0.5 and 1.2 mg/kg body weight.

20. The method of claim 13, wherein the compound is S-ethylisothiouronium diethylphosphate.

21. The method of claim 13, wherein the carrier or diluent comprises a sugar, a starch or cellulose preparation or a physiologically acceptable polymer and optionally includes a disintegrating agent or a salt thereof.

22. A method of alleviating nausea or vomiting resulting from the administration of an anticancer agent or treatment, the method comprising the step of administering to a subject in need thereof a therapeutically effective amount of a composition that comprises (a) a compound having the general formula:

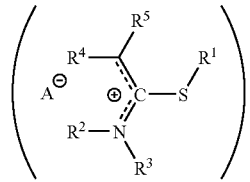

wherein,
R$_1$ is a linear or branched saturated or unsaturated alkylene, comprising one to eight carbon atoms optionally substituted with one or more substituent selected from the group consisting of halogen, primiary secondary or tertiary amine, primary, secondary or tertiary alcohol, or interrupted by one or more heteroatom selected from the aroup consisting of O, N, and S; R$_2$, R$_3$, R$_4$, and R$_5$ are each independently a hydrogen, hydroxy, liner or branched lower alkyl, linear or branched lower alkenyl, liner or branched lower alkynyl, lower alkoxy, alkoxyalkyl, cycloalkyl, cycloalkylalkyl, lower thioalkoxy, nitro, amino, cyano, sulfonyl, haloalkyl, carboaryloxy, carboalkylaryloxy, alkyl sulfoxide, aryl sulfoxide, alkyl sulfone, aryl sulfone, alkyl sulfate, aryl sulfate, sulfonamide, thioalkyl, optionally substituted by halogen;
A$^-$ is a physiologically acceptable anion, and (b) a pharmaceutically acceptable carrier or diluent; wherein the composition is administered together with or prior to the administration of the anti-cancer agent or treatment.

23. The method of claim 22, wherein the anticancer agent or treatment is selected from the group consisting of chemotherapy or radiotherapy.

24. The method of claim 22, wherein the carrier or diluent comprises a sugar, a starch or cellulose preparation or a physiologically acceptable polymer and optionally includes a disintegrating agent or a salt thereof.

* * * * *

UNITED STATES PATENT AND TRADEMARK OFFICE
CERTIFICATE OF CORRECTION

PATENT NO. : 7,148,208 B2
APPLICATION NO. : 10/382217
DATED : December 12, 2006
INVENTOR(S) : Barkan et al.

It is certified that error appears in the above-identified patent and that said Letters Patent is hereby corrected as shown below:

Column 22:
Lines 41-42, change "diethylphosohate; S-propylisothiourium" to -- diethylphosphate; S-propylisothiouronium --.
Line 66, after "wherein said" delete "wherein the".

Column 24:
Line 25, after "the group consisting of halogen," change "primiary" to -- primary --.
Line 28, before "consisting of O, N, and S;" change "aroup" to -- group --.
Line 29, after "are each independently a hydrogen, hydroxyl," change "liner" to -- linear --.

Signed and Sealed this

Twentieth Day of March, 2007

JON W. DUDAS
*Director of the United States Patent and Trademark Office*